United States Patent
McIver et al.

(10) Patent No.: US 6,932,982 B2
(45) Date of Patent: Aug. 23, 2005

(54) ENCAPSULATED FLAVOR AND/OR FRAGRANCE COMPOSITION

(75) Inventors: Robert C. McIver, Tabernacle, NJ (US); Florin Vlad, Annandale, NJ (US); Robert A. Golding, Jr., Plainsboro, NJ (US); Travis D. Leichssenring, Ewing, NJ (US); Daniel Benczedi, Carouge (CH)

(73) Assignee: Firmenich SA, Geneva (CH)

( * ) Notice: Subject to any disclaimer, the term of this patent is extended or adjusted under 35 U.S.C. 154(b) by 446 days.

(21) Appl. No.: 09/784,121

(22) Filed: Feb. 16, 2001

(65) Prior Publication Data

US 2002/0187223 A1 Dec. 12, 2002

(51) Int. Cl.⁷ .................................. A61K 9/14
(52) U.S. Cl. ................. 424/484; 424/485; 424/488
(58) Field of Search .................. 424/484, 485, 424/488

(56) References Cited

U.S. PATENT DOCUMENTS

| | | | |
|---|---|---|---|
| 3,704,137 A | 11/1972 | Beck | ........................... 99/140 |
| 4,232,047 A | * 11/1980 | Sair et al. | |
| 4,610,890 A | 9/1986 | Miller et al. | ................. 426/651 |
| 4,707,367 A | 11/1987 | Miller et al. | .................. 426/96 |
| 4,911,934 A | 3/1990 | Yang et al. | ................. 426/140 |

FOREIGN PATENT DOCUMENTS

| | | |
|---|---|---|
| EP | 0 202 409 A2 | 11/1986 |
| EP | 0 389 700 A1 * | 10/1990 |
| EP | 0 389 700 1 | 10/1990 |
| EP | 1 064 910 | 1/2001 |
| GB | 655 592 | 7/1951 |
| JP | 11190847 | 12/2000 |
| WO | 85/03414 * | 8/1985 |
| WO | WO 85/03414 | 8/1985 |
| WO | WO 94/06308 | 3/1994 |
| WO | WO/11589 | 4/1996 |
| WO | WO 99/27798 | 6/1999 |
| WO | WO 00/36931 | 6/2000 |

* cited by examiner

*Primary Examiner*—James M. Spear
*Assistant Examiner*—Humera N. Sheikh
(74) *Attorney, Agent, or Firm*—Winston & Strawn LLP

(57) ABSTRACT

The invention relates to a granular delivery system based on a matrix combining at least a carbohydrate material with from 1 to 7% of prehydrated agar agar. The system disclosed is particularly stable in aqueous environments and is capable of providing the controlled release of an active flavoring or perfuming ingredient there-encapsulated.

13 Claims, No Drawings

ENCAPSULATED FLAVOR AND/OR FRAGRANCE COMPOSITION

TECHNICAL FIELD

The present invention relates to the flavor and fragrance industry. It concerns more particularly an encapsulated system consisting of an extruded product, particularly stable in an aqueous environment and which is capable of releasing a flavoring or perfuming ingredient or composition in a controlled manner, under specific conditions such as for instance shear force or heat.

BACKGROUND OF THE INVENTION

Encapsulated systems represent an important issue for the flavor and fragrance industry.

Encapsulated systems are designed so as to achieve two kinds of objectives. The first goal typically sought is related to the function of protection of the ingredients covered by such systems. In fact, these systems must be capable of protecting an active material there-encapsulated from different types of "aggressions" such as oxidation or moisture. The stabilization of these systems constitutes therefore a critical issue in the field.

Another objective always targeted for an encapsulated system consists in controlling in an appropriate way (depending on the final application) the release of the active ingredient or composition encapsulated. In particular, in the case where the active ingredient is volatile, it may be of much importance to sustain and control its release during a prolonged period of time.

The complexity of such systems, as well as the variety of applications there-relate, justify a constant need to improve encapsulated systems and processes for making them so as to obtain products which satisfy all the requirements needed, such as a good stability under certain use conditions or an optimized controlled release of the encapsulate.

The prior art and in particular the patent literature describes a large number of encapsulated systems prepared by way of extrusion methods. Extrusion methods typically rely on the use of carbohydrate matrix materials which are heated to a molten state and combined with an active ingredient, before extruding and quenching the extruded mass to form a glass which protects said ingredient. Typical products issued from these methods and used in the flavor industry are dry, granular delivery systems in which the active ingredient is a flavor uniformly distributed as droplets throughout a carbohydrate glass.

One significant example of the prior art disclosure in this field is U.S. Pat. No. 3,704,137 which describes an essential oil composition formed by mixing an oil with an antioxidant, separately mixing water, sucrose and hydrolysed cereal solids with DE below 20, emulsifying the two mixtures together, extruding the resulting mixture in the form of rods into a solvent, removing the excess solvent and finally adding an anti-caking agent.

Another pertinent example is that described in U.S. Pat. No. 4,610,890 and U.S. Pat. No. 4,707,367 which disclose a process for forming a stable, melt based and extruded, solid, essential oil flavor composition, as well as a product of this process. The melt to be extruded consists, in this particular case, in a matrix formed of an aqueous mixture of a sugar and a starch hydrolysate together with a selected emulsifier, said aqueous mixture being further blended with a selected quantity of essential oil flavor. The above-mentioned patents, and all the other prior art there-cited, are merely illustrative of the considerable volume of patent literature related to the fixation of flavour ingredients in various matrices and which, in essence, discloses the encapsulation of flavour materials in glass-like polymeric materials, in particular carbohydrate matrices.

A large variety of matrix components are disclosed in this prior art and play a part in the release process of these systems. In the case of systems based on the use of carbohydrate materials, said carbohydrates dissolve almost instantly in the presence of water, thus releasing the flavor into the aqueous environment. Complete dissolution and flavor liberation occur in less than 1 minute and may last up to 2 minutes, depending on the exact composition of the matrix.

Now, in applications where water is present, a better retention of a flavor within a particle may be needed. Similarly, the field of perfumery embraces many applications where a prolonged diffusion of the perfuming ingredient or composition through the particles may be desired.

Some methods to achieve those effects are known and generally consist in making particles with an insoluble surface (coacervation, coating with a fat). However, said techniques require an additional step (coating) and do not provide optimal results.

Now, the present invention offers a product with a retarded flavor or fragrance release in water, and which is an improvement of standard extrusion technology such as disclosed in the above-mentioned patent literature as well as in other documents cited below. In fact, we have now been able to realize a novel granular i.e. extruded system capable of controlling the release of an active ingredient, in particular in an aqueous environment. Said system is based on the use of agar agar in the matrix composition.

Amongst the large number of materials disclosed in the prior art as being potentially useful in matrix compositions of encapsulated systems, agar agar is often cited and used either as a coating material, or as a binder or granulating agent.

Agar agar is part of the family of hydrocolloids, also referred as gums. Hydrocolloids are long-chain high molecular weight polymers that disperse and hydrate in water to give a thickening and sometimes a gelling effect.

A large amount of the patent literature related to encapsulated systems cites agar agar as part of the possible encapsulation materials. For instance, WO 99/27798, which describes improved chewing gum formulations including sodium bicarbonate and Aspartame® in an encapsulated form, discloses agar agar in a list of coating ingredients, said list also comprising in particular dextrin, modified starch, acacia or maltodextrin. On the other hand, agar agar is also cited in some documents as being used as a granulating agent. In particular, U.S. Pat. No. 4,911,934, which also describes a chewing gum composition including encapsulated sweeteners and having an extended flavor release, discloses the use of agar agar as a granulating agent, capable of causing agglomeration or aggregation of the sweetening agent particles.

Therefore, agar agar has a widespread use in foods as stabilizer, thickener, humectant and surface finisher. Like many other colloids, agar agar also has film forming and bioadhesive properties. However, although other hydrocolloids are frequently cited in specific examples of the patent literature, agar agar only appears as part of the all encompassing list of gums, hydrocolloids, film forming agents and bioadhesives and is disclosed generally as a possible useful material, but not specifically exemplified.

Yet, we have now been able to establish that, in combination with a carbohydrate material and when used in far smaller amounts than those disclosed in the prior art, agar agar is a very useful matrix material and provides particularly advantageous effects on extruded systems, stabilising them in an aqueous environment and improving the retention of the active ingredient or composition there-encapsulated.

BRIEF SUMMARY OF THE INVENTION

The present invention thus relates to a granular delivery system comprising a flavor or fragrance ingredient or composition distributed as droplets throughout a matrix of polymeric carriers, wherein said carriers comprise at least a carbohydrate material and from 1 to 7% of agar agar, based on the dried weight of the granular system, i.e. of the extruded product.

The system of the present invention presents many advantages. In particular, the incorporation of agar agar in such specific proportions advantageously prevents the release of the flavor or fragrance ingredient or composition, hereafter referred to as the "active" ingredient in an aqueous environment. In fact, in the presence of water, the delivery system of the invention, in the form of particles, rehydrates and rapidly forms an agar agar-carbohydrate gel structure which physically traps the active ingredient, usually in the form of oil droplets. In the case where a flavor ingredient is encapsulated, the system of the present invention allows the retention of the flavor within the particles in applications where water is present, until shear or heat are applied to cause release of the active ingredient. The system is thus very advantageous in applications such as chewing gums and soft chewy confections or ice creams for instance. In particular, chewy sweets constitute the most typical example in which the carrier is expected to release the active ingredient only upon chewing, thus providing flavor hot spots and further avoiding an early exposure of the flavor to the fats contained in these products.

In the case of fragrances, the diffusion of the active ingredient from the particles may take several hours depending on the external environment (surfactant for instance) and the invention thus provides an interesting controlled release system, in applications such as detergents or fabric softeners in particular.

On the other hand, the composition of the matrix according to the present invention is adapted, from a process point of view, to be extruded according to usual techniques. By "usual extrusion techniques", we mean here methods according to which, typically, an aqueous carbohydrate melt, the active material and an optional emulsifier are allowed to form an homogeneous emulsion, which is extruded under pressure through a die plate and then cooled to form a solid product containing the active material, dispersed as fine droplets.

A large number of particular embodiments of this general method are described in the varied patent literature related to extrusion techniques and may be used for processing a matrix according to the invention. Some of these processes will be described in a more detailed manner below.

The active materials advantageously encapsulated according to the invention can be selected among all the current flavour and fragrance materials, which are preferably hydrophobic. Hydrophilic components may also be used, but their release may be less retarded as a function of their partition in the outer aqueous environment. The examples given hereafter are meant to illustrate a variety of embodiments of the invention but are not to be interpreted as limiting the latter.

More objects, aspects and advantages of the invention will become apparent from the detailed description hereafter.

DETAILED DESCRIPTION OF THE INVENTION

It has been unexpectedly discovered that agar agar can be advantageously used in very small amounts, in combination with a carbohydrate material, in the composition of the matrix of an extruded system, said system being consequently stable for a prolonged period in water, and releasing in a controlled manner the active ingredient there-encapsulated.

As previously cited, one object of the present invention is to provide a granular delivery system comprising a flavor or fragrance ingredient or composition dispersed as droplets throughout a matrix of polymeric carriers, wherein said carriers comprise at least a carbohydrate material and from 1 to 7% of agar agar. The percentage of agar agar as well as all the proportions mentioned below are given by weight relative to the dried weight of the extruded product. The agar agar used in the invention is in a prehydrated form.

The system of the invention is particularly advantageous when used in an aqueous environment. In fact, the specific combination of a carbohydrate material with agar agar in the above-cited range of concentrations unexpectedly allows the formation of a gel barrier which prevents the granules from an immediate dissolution in water as it was the case in the prior art, thus providing a slow release of the flavor or fragrance droplets. The invention advantageously provides a system showing a high percentage of retention of the active ingredient there-encapsulated after the particle rehydration, while being easy to manufacture with standard manufacturing equipment.

It is particularly surprising to observe the effectiveness of agar agar at such a low concentration and at the same time its advantages from a process point of view, as heretofore, in extrusion processes for example, the viscosity constitutes a limiting factor of the amount of gum that can be incorporated. The range of concentration of agar agar is totally unexpected and represents an essential characteristic of the invention.

The matrix of the delivery system according to the present invention comprises at least the above-mentioned combination, namely a carbohydrate material and from 1 to 7% of agar agar. Preferably it contains from 1 to 3% and more preferably from 1 to 1.5% of agar agar. The proportions of carbohydrate material are usually comprised between 0 and 95% relative to the dried extruded product, and preferably between 40 and 90%.

As the carbohydrate material used in combination with agar agar in the delivery system of the invention, there can be used any sugar or sugar derivative which can be readily processed through extrusion techniques to form a dry extruded solid. Particular examples of suitable materials include those selected from the group consisting of sucrose, glucose, lactose, levulose, fructose, maltose, ribose, dextrose, isomalt, sorbitol, mannitol, xylitol, lactitol, maltitol, pentatol, arabinose, pentose, xylose, galactose, hydrogenated starch hydrolysate or succinylated, chemically modified starch, corn syrup, maltodextrin, polydextrose and derivatives and mixtures thereof.

In one particular embodiment of the invention, the carbohydrate material is selected from the group consisting of maltodextrin or a corn syrup, a chemically modified starch, a hydrogenated starch hydrolysate or a succinylated or hydrolyzed starch. Preferably, the maltodextrin used has a dextrose equivalent (DE) of at least 18.

Following specific embodiments, there will be used polymeric carriers which include maltodextrin. The latter can be the main carbohydrate material of the matrix, or yet, be used in admixture with any one of the sugars mentioned above, preferably sucrose.

In another embodiment, the polymeric carrier consists of maltodextrin in the form of a narrow cut of polymer chains (Glucidex® C1872; origin: Roquette America, Inc. Keokuk, Iowa, USA) and from 1 to 7% of agar agar.

The active ingredient encapsulated in the system according to the invention will preferably be a hydrophobic flavor or fragrance ingredient or composition of current use. However the polarity or aqueous solubility of the active ingredient may be chosen as a function of the desired retardation of the release for a given application. In fact more hydrophilic components will be released faster as they are able to partition in the outer aqueous environment.

The terms flavor or fragrance ingredient or composition as used herein are deemed to define a variety of flavor and fragrance materials of both natural and synthetic origin. They include single compounds and mixtures. The system of the invention may encapsulate volatile or labile components which may be in liquid or solid form, preferably hydrophobic. Specific examples of such components may be found in the current literature, e.g. in Perfume and Flavour Chemicals by S. Arctander, 1969, Montclair N.J. (USA); Fenaroli's Handbook of Flavour Ingredients, 1975, CRC Press or Synthetic Food Adjuncts, 1947, by M. B. Jacobs, van Nostrand Co., Inc. and are well-known to the person skilled in the art of perfuming, flavoring and/or aromatizing consumer products, i.e. of imparting an odor and/or a flavor or taste to a consumer product traditionally perfumed or flavored, or of modifying the odor and/or taste of said consumer products.

Natural extracts can also be encapsulated into the system of the invention; these include e.g. citrus extracts such as lemon, orange, lime, grapefruit or mandarin oils, or coffee, tea, cocoa, mint, vanilla or essential oils of herbs and spices, amongst other.

The proportion of active ingredient in the matrix is comprised between 0.1 and 25% by weight relative to the dried extruded product, and preferably between 5 and 16%.

An emulsifier agent may be added to the mixture constituted by the matrix components and the active ingredient, in proportions varying typically from 0.1 to 10%, and preferably from 0.4 to 2%, relative to the solid product. Typical examples include soya lecithin and citric acid esters of fatty acids, but other suitable emulsifiers are cited in reference texts such as Food Emulsifiers and Their Applications, 1997, edited by G. L. Hasenhuettl and R. W. Hartel, USA.

Other additional ingredients of current use in the art of extruded products may be added to the matrix such as free flow agents, or coloring materials, both natural or artificial.

Typically, the final products have a moisture content comprised between 2 and 8%.

The system of the present invention shows an unexpected and advantageous behavior in an aqueous environment, which can be displayed during a rehydration process. In fact, while a classical encapsulation system such as disclosed in the prior art, represented for example by U.S. Pat. No. 4,610,890 or U.S. Pat. No. 4,707,367, would dissolve instantly or rapidly in water, thus releasing immediately the active ingredient oil droplets, the granules according to the invention, due to the formation of a more or less strong gel, prevent the instant release of the oil. During a rehydration process, a gel layer is rapidly formed at the surface of the product. Once the initial layer is formed, no loss of flavor or fragrance oil droplets can occur into the surrounding water. There does not appear to be coalescence of the oil droplets. After complete rehydration in typically 4 to 5 min., the particle is a flexible gel. Strong pressure applied to the particle results in the breakage into smaller gelled pieces. Flavor or fragrance oil is released at the fracture point only.

Another object of the present invention is a process for the preparation of a delivery system as defined above, comprising the basic steps of a) combining and blending a flavour or fragrance ingredient or composition with a matrix comprising an aqueous solution of at least a carbohydrate material, from 1 to 7% of agar agar and optionally an emulsifier, under temperature and stirring conditions useful to produce a uniform melt thereof;

b) extruding the uniform melt through a die;

c) chopping, cutting, grinding or pulverising the material obtained as it exits the die or after cooling the melt; and d) optionally drying.

In the process of the invention, agar agar is used in a prehydrated form.

The process above-described embraces a variety of extrusion techniques, depending notably on the materials used and on the amount of water added in the first step of the process, which may have to be reduced during a drying step in order to obtain a final product having an acceptable glass transition temperature (Tg). In fact, the critical glass transition temperature may be at least above 20° C. and preferably above 40° C. for the major part of applications. However in some cases, it may be useful to prepare delivery systems which have glass transition temperatures below ambient temperature as disclosed in WO 96/11589, the content of which is hereby included by reference. The proportions in which water is employed in the present invention therefore vary in a wide range of values which the skilled person is capable of adjusting and choosing as a function of the carbohydrate glass used in the matrix and the required Tg of the final product.

According to one particular embodiment, typical conditions for this process are similar to those described for example in U.S. Pat. No. 3,704,137, the contents of which is hereby included by reference. More particularly, in step a), the carbohydrate material is mixed with a sufficient amount of water and heated to form a solution. Separately, the agar agar is mixed with approximately 11 times its weight in water and allowed to rehydrate. The agar agar suspension is then added to the carbohydrate solution which is then heated to remove sufficient water to form a viscous melt containing from 3 to 12% of water. The active ingredient and an optional emulsifier are then mixed with the melt under high shear to uniformly disperse the active ingredient throughout the melt. In another embodiment, the agar agar suspension is added to the preformed emulsion consisting of the active ingredient dispersed as droplets in the carbohydrate matrix. This is then extruded under pressure through a die plate (step b)) and falls into a chilled solvent where the material is cooled to a glass, chopped and the surface washed of actives (step c)). The particles are then dried to remove residual solvent and reduce the moisture content to from 2 to 8%. The shape and size of the extruded solid can be adjusted as a function of the extrusion parameters. The temperature and pressure conditions under which this process is carried out are current and fully described in the US document cited above, the teaching of which is hereby included by reference and forms an integral part of the present specification. Such parameters can therefore be adjusted by the skilled person without particular effort and as a function of the nature of the ingredients present in the melt and of the quality of the product which is desired to obtain, i.e. its granulometry and shape. The type and design of the equipment used require no detailed description here, the expert in this field being well-acquainted with current apparatuses, their technical specificities and the choice of appropriate equipment for a desired specific shape and size of the extruded solid. It is well-known, moreover, that such extruded solids may be produced in many forms, i.e. powders of varied granulometry, rods, flakes, filaments, etc. Techniques such as grinding (or criogrinding), pulverising or sieving are also known to further provide for reduction of the size of the extruded solid, namely in the case of extruded particulate solids, to reduce it to the state of fine micromized powders, if so desired.

Another kind of extrusion technique suitable according to the present invention, namely wet-granulation, is described in EP 202409, the content of which is included herewith by reference. This method also comprises step d) of the above-mentioned process, namely a drying step. More particularly, this document discloses a method for the production of stable, spherical particles of viable micro-organisms which comprises the steps of mixing a culture concentrate with a bulking agent to form a homogeneous wet granulate, extruding the wet granulate through a die to produce filaments having a diameter of approximately the size of the desired spheres and then using a spheroniser device which comprises a plate that rotates at a tangential speed sufficient to cause the filaments to be shaped into discrete spherical particles, and finally drying the particles. Before the drying step, the glass transition temperature of the extruded mass is relatively low because of the large proportion of water used as plasticiser. The additional drying step is thus necessary to evaporate some water from the system, thus increasing the Tg to a sufficient value to provide a product capable of being stored at room temperature.

According to another extrusion method suitable for the instant invention, the drying step may be avoided. In that case, there is no need to first blend the hydrophilic active material and the matrix materials with a large amount of water to obtain a homogeneous melt. It is possible in fact to heat a substantially solid mixture of these ingredients, containing only a small amount of plasticiser, to its glass transition temperature, and to press-feed the extruder with this substantially solid mass, under efficient mixing, to ensure formation of an homogeneous melt and obtain a stable extruded product. The so-called "dry-blend" extrusion techniques obey this principle, and they typically require the use of higher pressures to feed the melt of the originally essentially solid material through the extruder than the methods cited above which resort to the extrusion of substantially liquid or fluid mixtures of ingredients.

Thus, in the processes described in the above-mentioned literature and in the prior art in general, which are adapted to the present invention, the homogeneous mixture of active ingredient and carbohydrate matrix prepared in the first step of the process is heated within a screw-extruder in such a way that the temperature of the mixture is above the glass transition temperature of the matrix in order to form a molten mass. Then, the molten mass is extruded through a die.

Step c) of the process depends on the technique used. In the first technique described here-above (notably disclosed in U.S. Pat. No. 3,704,137), the molten mass can be cooled as it exits the die to a temperature below the glass transition temperature of the matrix. Extruded granules can be manufactured by breaking the extruded material cooled below its glass transition temperature. This crushing step unavoidably loses a certain amount of matter because of the hardness of the material and it can also happen that the encapsulated volatile compound is damaged and partially lost during this step.

In other cases, wet-granulation or melt granulation is used to chop the extruded product as it is still in a plastic state above its glass transition temperature.

According to the last extrusion technique above-described, wherein the matrix contains a small amount of water, there are provided solid delivery systems which are prepared via a process according to which the uniform melt produced in step a) is obtained by heating the mixture of matrix carbohydrate material, agar agar and active ingredient to a temperature comprised between 90 and 130° C., the mixture being then subsequently extruded trough a die and the molten mass being chopped as it exits the die and before it is cooled to solidify.

According to this particular embodiment, a low water content is added to the mixture to be melt to guarantee that the glass transition temperature Tg of the resulting melt corresponds to, and is substantially the same as, that of the desired Tg value of the final product. In other words, contrary to other methods such as wet-granulation, the glass transition temperature of the mixture before extrusion has already the value required for the final product, which temperature is above 20° C. and preferably above 40° C. so that the product can be stored at ambient temperature in the form of free-flowing granules. As a consequence, this embodiment of the invention can dispense with the additional drying step following the extrusion, intended to remove water in order to increase Tg to an acceptable value. Moreover, the extruding step of this process requires an extruding apparatus. A commercially acceptable extruding apparatus is that under the trade name designation of Clextral BC 21 twin-screw extruder equipped with a cutterknife allowing to chop the melt at the die exit, when it is still plastic. However, extruding apparatuses are not limited to the twin screw variety and may also include, for example, single screw, ram, or other similar extrusion methods. The extrusion apparatus is equipped with a temperature regulation mechanism allowing to increase progressively the temperature of the mixture up to a value comprised typically between 90 and 130° C., at which point it can be extruded through a die.

The instant extruded solids resulting from any embodiment of the process according to the invention can be advantageously used to impart or modify the organoleptic properties of a great variety of edible or perfumed end products. In the field of flavors, these consumer products may include foods, beverages, pharmaceuticals and the like. The incorporation of granules according to the invention in chewing gums or soft chewy confections, tooth-pastes and ice-creams is straightforward and provides improved effects. On the other hand, in the field of perfumery, the granular solids according to the invention may be advantageously incorporated in a perfuming composition added to functional products such as detergents or fabric softeners. For instance, during a textile wash cycle, the granules will release the active perfuming ingredient or composition in a controlled manner, thus imparting to the textile a desired odor for a prolonged period of time.

The releasing effect of the extruded products of the invention can also be advantageously employed in other functional applications such as soaps, bath or shower gels, deodorants, body lotions, shampoos or other hair-care products, household cleansers, cleaning and deodorizing blocks for toilet tanks. These examples are of course not exhaustive and are not restrictive of the invention.

The concentrations in which the extruded solids can be incorporated in such consumer products vary in a wide range of values, which are dependent on the nature of the product to be flavored or perfumed. Typical concentrations, to be taken strictly by way of example, are comprised in a range of values as wide as from a few ppm up to 5 or even 10% of the weight of the flavoring or perfuming composition or finished consumer product into which they are included.

Adjuvants such as for example food grade colorants can also be added in a generally known manner, to the extrudable mixtures of the invention, so as to provide colored flavor or perfume systems and granulates.

The invention will now be illustrated by way of the following examples but is not limited to these examples. Temperatures are given in degrees centigrade and abbreviations have the meaning common in the art.

EMBODIMENTS OF THE INVENTION

Example 1

Preparation of a Granular Delivery System According to the Invention

A matrix formulation was prepared with the following ingredients

| Ingredients | Grams | % dry |
|---|---|---|
| Maltodextrin 18 DE | 1300 | 41.50 |
| Sucrose | 1300 | 41.50 |
| Cinnamic aldehyde | 470 | 15.00 |
| Agar agar[1] | 31 | 1.0 |
| Soya lecithin[2] | 31 | 1.0 |
| Water | 800 | |
| Total | | 100.00 |

[1]origin: TIC Gums Inc., Belcamp, Maryland, USA
[2]origin: Central Soya, Fort Wayne, Indiana, USA The agar agar was mixed with 400 g of water to form a slurry. This was added to a syrup made from the sucrose, maltodextrin and 400 g of water. The mixture was heated to 123° to reduce the moisture content of the syrup. The cinnamic aldehyde and emulsifier were mixed with the concentrated syrup with high shear to form a uniform melt which was then extruded under $2 \times 10^5$ Pa pressure through a die plate with 0.8 mm diameter holes into a cold solvent for chilling and breaking of the strands. After drying, 0.5% silicon dioxide was added as free flow agent. The resulting product contained 13.6% by weight of cinnamic aldehyde, 5.7% moisture and had a glass transition temperature of 34°.

When 50 g of particles were placed in 500 ml of water, the particles swelled to approximately 3 times their original volume. After 4 days in water, the soft gelled particles were found to contain 13.1% cinnamic aldehyde by weight (based on the original dry weight of the particles).

Example 2

Preparation of a Granular Delivery System According to the Invention

A matrix formulation was prepared by admixing the following ingredients

| Ingredients | Grams | % dry |
|---|---|---|
| 18 DE maltodextrin syrup[1] | 4459 | 81.50 |
| Fragrance | 630 | 16.00 |
| Soya lecithin[2] | 39 | 1.00 |
| Agar agar | 59 | 1.50 |
| Water | 400 | — |
| Total | | 100.00 |

[1]Glucidex ® C 1872, 72% solids; origin: Roquette America, Inc., Keokuk, Iowa, USA
[2]Origin: Central Soya, Fort Wayne, Indiana, USA The agar agar was mixed with 400 g of water to form a slurry which was then mixed into the maltodextrin syrup. Further processing steps were the same as described in Example 1.

The final granules were found to contain 14.5% fragrance, 6.3% moisture and have a glass transition temperature of 66°.

When 50 g of the particles were placed in 500 ml of water, the particles swelled to approximately 2 times their original volume. After 5 days in water, the soft gelled particles were found to contain 14.1% fragrance by weight (based on the original dry weight of the particles).

Example 3

Preparation of a Granular Delivery System According to the Invention

A matrix formulation was prepared by admixing the following ingredients

| Ingredients | Grams | % dry |
|---|---|---|
| Hydrogenated Starch Hydrolysate[1] | 4278 | 88.00 |
| Cold pressed Valencia orange oil | 350 | 10.00 |
| Emulsifier[2] | 18 | 0.50 |
| Agar agar | 53 | 1.50 |
| Water | 350 | — |
| Total | | 100.00 |

[1]Polysorb ® C 1895 68% solids; origin: Roquette America, Inc., Keokuk, Iowa, USA
[2]see Example 1.

The particles were prepared according to the method described in Example 2. The final product contained 9.7% of orange oil on a weight basis and 7.5% moisture.

When 50 grams of the particles were placed in 500 ml of water, the particles swelled to approximately 1.5 times their original volume. After 5 days in water, the soft gelled particles were found to contain 9.1% orange oil by weight (based on the original dry weight of the particles).

Example 4

Preparation of a Granular Delivery System According to the Invention

A matrix formulation was prepared by admixing the following ingredients

| Ingredients | Grams | % dry |
|---|---|---|
| 18 DE maltodextrin | 1505 | 43.00 |
| Sucrose | 1505 | 43.00 |
| Menthol crystals | 438 | 12.50 |
| Emulsifier | 18 | 0.50 |
| Agar agar | 35 | 1.00 |
| Water | 800 | — |
| Total | | 100.00 |

The particles were prepared according to the method described in Example 1. The final product contained 10.5% menthol on a weight basis and 5.4% moisture.

When 50 grams of the particles were placed in 500 ml of water, the particles swelled to approximately 3 times their original volume.

For all the systems prepared, moisture determination of finished products was done by Karl Fisher titration. Flavor content of products was assayed by steam distillation or gas chromatography. Flavor retention after 5 days in water was determined by rehydrating 50 g of granules sized 250–850 μm in 500 ml of water in a shallow covered dish. After 5 days in water, the gel particles were filtered on a 250 μm mesh screen and washed with 200 ml of water. Both the washed particles and filtrate were steam distillation for oil content.

The rehydration properties of the particles were examined by light microscopy.

The gelled particles appear to be stable over time as indicated by the fact that over 90% of the oil in the particles remained after sitting for 5 days in water.

Example 5
Comparative Example on a Rehydration Test

Four batches were prepared according to respectively Example 1, 2, 3 and 4, hereafter respectively referred as B1, B2, B3 and B4. For comparison, a fifth batch was prepared according to the process described in Example 1, by admixing the following ingredients:

| Ingredients | Grams | % dry |
|---|---|---|
| Maltodextrin 18 DE | 1505 | 44.55 |
| Sucrose | 1505 | 44.55 |
| Cold pressed Valencia orange oil | 350 | 10.36 |
| Soya lecithin[1)] | 18 | 0.54 |
| Water | 400 | — |
| Total | | 100.00 |

[1)]origin: Central Soya, Fort Wayne, Indiana, USA

Moisture determination of the finished products was carried out by Karl Fisher titration. Flavour content of the products was assayed by steam distillation or gas chromatography. Flavour retention after 5 days in water was determined by rehydrating 50 g of granules sized 250–850 $\mu$m in 500 ml of water in water in a shallow cover dish. After 5 days in water, the gel particles were filtered on a 250 $\mu$m mesh screen and washed with 200 ml of water. Both the washed particles and filtrate were steam distilled for oil content.

The rehydration properties of the particles were examined by light microscopy.

Table I reports the results of these measurements:

TABLE I

| Batch Number | Percentage of oil retention after 5 days in water | Rehydration observations |
|---|---|---|
| B1 | 96.3 | Swells to 3 times volume Soft gel formed |
| B2 | 97.2 | Swells to 2 times volume Soft gel formed |
| B3 | 93.8 | Swells to 1.5 times volume Soft gel formed |
| B4 | 92.2 | Swells to 3 times volume Soft gel formed |
| B5 | 0 | Dissolution in 60 s in water No gel formed |

We claim:

1. Process for the preparation of a delivery system comprising a flavor or fragrance ingredient or composition distributed as droplets throughout a matrix of polymeric carriers, wherein said carriers comprise at least a carbohydrate material and from 1 to 7% of prehydrated agar agar, relative to the dried weight of the granular system, and the process comprising the following steps:
   combining and blending a flavour or fragrance ingredient or composition with a matrix comprising an aqueous solution of at least a carbohydrate material, from 1 to 7% of prehydrated agar agar, and optionally an emulsifier, under temperature and stirring conditions useful to produce a uniform melt thereof;
   extruding the uniform melt with a screw-extruder through a die;
   chopping, cutting, grinding or pulverising the material obtained as it exits the die or after cooling the melt; and
   optionally drying.

2. Process according to claim 1, wherein the matrix consists of a hot carbohydrate melt of 4 to 12% moisture.

3. Process according to claim 1, wherein step d) is followed by the mixing of the obtained particles with a free flow agent.

4. Process according to claim 1, wherein the carriers comprise from 1 to 3% of agar agar.

5. Process according to claim 1, wherein the carriers comprise from 1 to 1.5% of agar agar.

6. Process according to claim 1, wherein the flavor or fragrance ingredient or composition is hydrophobic.

7. Process according to claim 1, wherein the carbohydrate material is selected from the group consisting of a maltodextrin or corn syrup, a chemically modified starch, a hydrogenated starch hydrolysate or a succinylated or hydrolysed starch.

8. Process according to claim 1, wherein the carriers consist of maltodextrin in the form of a narrow cut of polymer chains and from 1 to 7% of agar agar.

9. Process according to claim 1, wherein the carriers consist of maltodextrin in the form of a narrow cut of polymer chains and from 1 to 3% of agar agar.

10. Process according to claim 1, wherein the polymeric carriers further comprise a sugar, selected from the group consisting of sucrose, glucose, lactose, maltose, fructose, isomalt, sorbitol, mannitol, xylitol, lactitol, maltitol, and hydrogenated corn syrup.

11. Process according to claim 1, wherein the carbohydrate material comprises maltodextrin that has a dextrose equivalent equal to or above 18.

12. Process according to claim 1, wherein the flavor or fragrance ingredient or composition represents from 0.1 to 25% by weight relative to the dried granular system.

13. Process according to claim 1, wherein the flavor or fragrance ingredient or composition represents from 5 to 16% by weight relative to the dried granular system.

* * * * *